US00PP23699P2

(12) United States Plant Patent
Welsh

(10) Patent No.: US PP23,699 P2
(45) Date of Patent: Jul. 2, 2013

(54) ***EUCOMIS* PLANT NAMED 'EUW061'**

(50) Latin Name: *Eucomis comosa*
Varietal Denomination: EUW061

(76) Inventor: Eddie Welsh, Palmerston North (NZ)

( * ) Notice: Subject to any disclaimer, the term of this patent is extended or adjusted under 35 U.S.C. 154(b) by 130 days.

(21) Appl. No.: 13/200,512

(22) Filed: Sep. 23, 2011

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Howard Locker
(74) *Attorney, Agent, or Firm* — Cassandra Bright

(57) ABSTRACT

A new and distinct *Eucomis* cultivar named 'EUW061' is disclosed, characterized by unique pink flowers that become darker pink with age. The new variety has a compact growth habit attractive dark pink scape. The new variety is a *Eucomis*, normally produced as an ornamental garden or container plant.

2 Drawing Sheets

Figure 1:
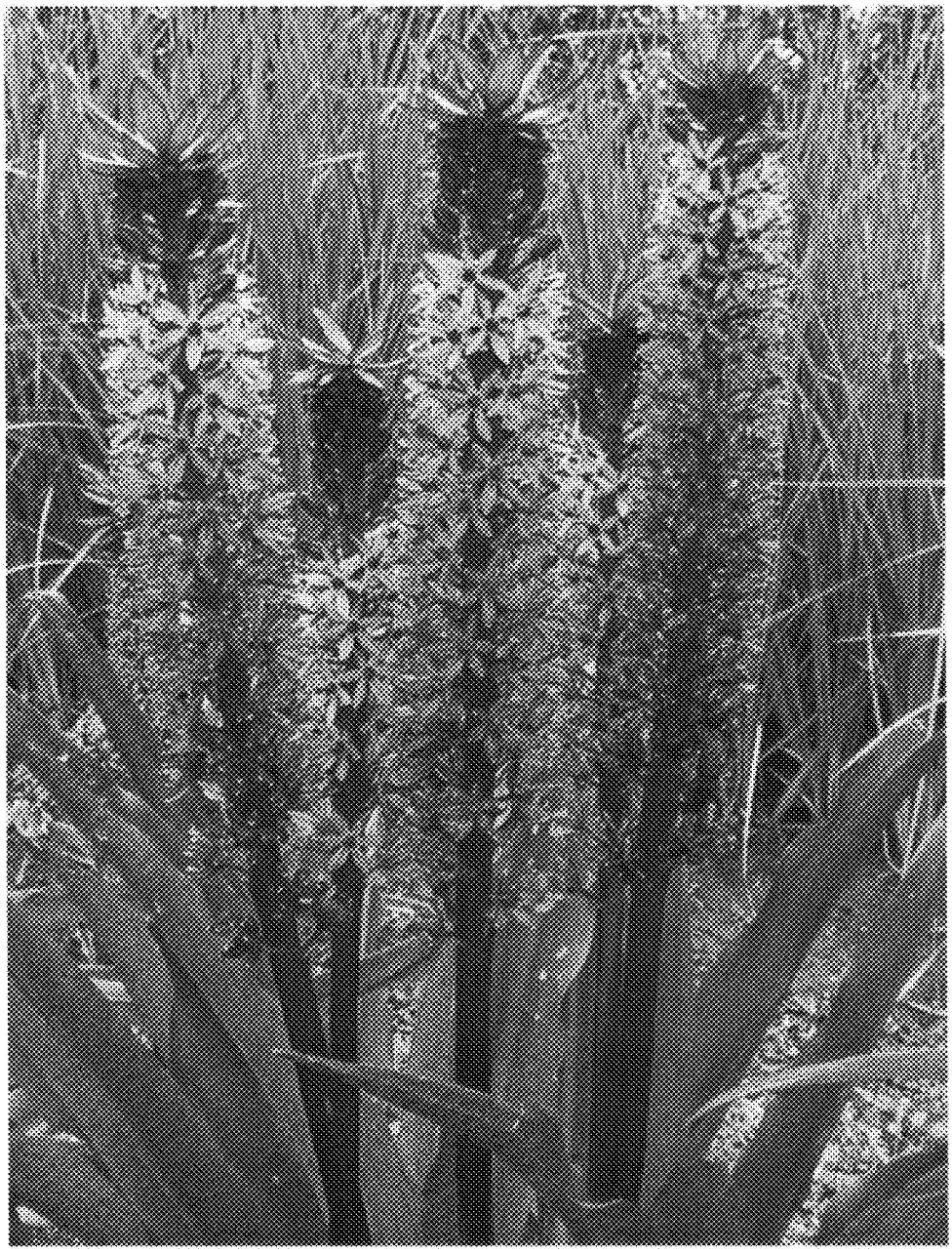

Latin name of the genus and species: *Eucomis comosa.*
Variety denomination: 'EUW061'.

BACKGROUND OF THE INVENTION

The new *Eucomis* cultivar is a product of a planned breeding program conducted by the inventor, Eddie Welsh, in Palmerston North, New Zealand. The objective of the breeding program was to produce new *Eucomis* varieties for ornamental commercial applications. The cross resulting in this new variety was made during January 2001.

The seed parent is an unnamed, unpatented, proprietary seedling of *Eucomis comosa*. The pollen parent is unknown, as the crossing resulting in 'EUW061' was an open pollination, with unidentifiable pollen parents. The new variety was discovered in February 2004 by the inventor in a group of seedlings resulting from the 2001 crossing, in a commercial nursery in Palmerston North, New Zealand.

Asexual reproduction of the new cultivar 'EUW061' by tissue culture was first performed at a commercial laboratory in Auckland, New Zealand in 2006. Plants were kept confidentially in the laboratory, with limited access, and only supplied to the inventor. Subsequently, 'EUW061' has also been reproduced by leaf and bulb scale cuttings, also confidentially and without access by the public to plant material. Asexual propagation by the above referenced means has shown conclusively that the characteristic and unique features of this cultivar are stable and are reproduced true to type in successive generations.

SUMMARY OF THE INVENTION

The cultivar 'EUW061' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EUW061' These characteristics in combination distinguish 'EUW061' as a new and distinct *Eucomis* cultivar:

1. Unique pink flower color.
2. Attractive flower color change with age, becoming deeper pink.
3. Dark pink scape coloration.

Plants of the new cultivar 'EUW061' are similar to plants of the seed parent, in most horticultural characteristics, however, plants of the new cultivar 'EUW061' produce flowers of a different color, and also different colored scapes.

COMMERCIAL COMPARISON

Plants of the new cultivar 'EUW061' are comparable to the variety *Eucomis comosa* 'Sparkling Burgundy', unpatented. The two *Eucomis* varieties are similar in most horticultural characteristics, however, the new variety 'EUW061' differs in having flowers that are more pure pink, without the greenish tinge found in 'Sparkling Burgundy'. Additionally, plants of 'EUW061' are shorter, more compact plant with more green tones in the foliage.

Plants of the new cultivar 'EUW061' can also be compared to the commercial variety *Eucomis* 'Reuben', unpatented. These varieties are similar in most horticultural characteristics, however 'EUW061' has darker pink colored flowers, a darker pink scape, darker colored foliage and an overall smaller plant habit.

BRIEF DESCRIPTION OF THE PHOTOGRAPHS

The accompanying photograph in FIG. 1 illustrates in full color a typical plant of 'EUW061' grown outdoors, in the ground. Age of the plant photographed is approximately 3 years from a bulb.

Figure 2:
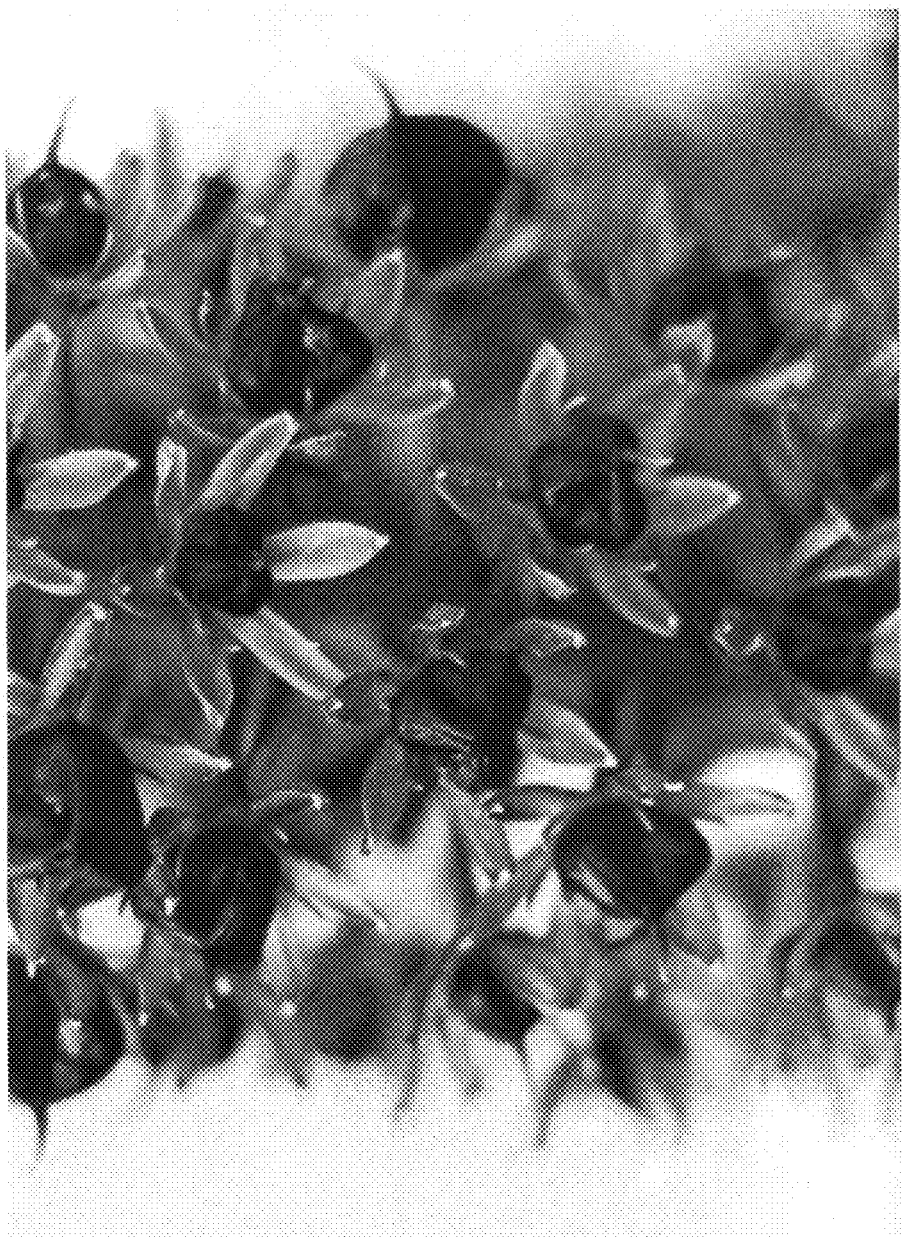

FIG. 2 illustrates in full color a close up of a typical seed pods of 'EUW061'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'EUW061' plants grown in a greenhouse, and moved outdoors during Spring Palmerston North, New Zealand. The growing temperature ranged from 15° C. to 30° C. during the day and from 8° C. to 15° C. during the night. General light conditions are bright, normal sunlight. Measurements and numerical values represent averages of typical plant types. Plants are approximately 3 years old from a bulb.

Botanical classification: *Eucomis comosa* 'EUW061'.

PROPAGATION

Time to initiate roots: About 45 days at approximately 16° C.

Root description: Thick, fleshy. Colored near White N155C.

PLANT

Age of plant described: Approximately 3 years from a bulb.

Growth habit: Compact, irregular rosette forming flowering bulbous perennial.

Height: Approximately 61 cm to the top of the foliar plane.

Plant spread: Approximately 52 cm.

Normal pot size: 1 gal.

Growth rate: Rapid.

Branching characteristics: Irregular rosette formation, eventually forming 4-6 side planlets/bulblets.

FOLIAGE

Leaf:

- *Arrangement*.—Basal Rosette.
- *Quantity per plant*.—6 per main bulb.
- *Average length*.—Approximately 38 cm.
- *Average width*.—Approximately 7.5 cm.
- *Shape of blade*.—Strap.
- *Aspect*.—Outward arch and upwardly cupped.
- *Apex*.—Acuminate.
- *Base*.—Clasping, sheathing. Sheath length: Average 6 cm. Sheath width: Average 1.5 cm.
- *Margin*.—Entire.
- *Texture of top surface*.—Smooth, shiny.
- *Texture of bottom surface*.—Smooth.
- *Color*.—Young foliage upper side: Near RHS Yellow-Green 146A margin Near Red-Purple 59B. Young foliage under side: Near RHS Yellow-Green146B margin Near Red-Purple 59B. Mature foliage upper side: Near RHS Yellow-Green 147A margin Near Red-Purple 59B. Mature foliage under side: Near RHS Yellow-Green 147B margin Near Red-Purple 59B.
- *Venation*.—Type: Parallel. Venation coloration: Near Yellow-Green 147A, but, darker.

FLOWER

Inflorescence description: Terminal racemes; numerous actinimorophic flowers, segments free, fused tube, flowers face outwardly.

Natural flowering season: Summer.

Days to flowering from bulb or plantlet: 150 days.

Rate of flower opening (individual): 2 to 3 days from bud to fully opened flower.

Rate of flower opening (inflorescence): 14-21 days from bud to all flowers open.

Inflorescence longevity on plant: 120 days.

Inflorescence height, excluding scape: Approximately 32 cm.

Inflorescence width: Approximately 6 cm.

Individual flower quantity per inflorescence: Approximately 100.

Persistent or self-cleaning: Persistent.

Fragrance: Slightly sweet.

Individual flowers:

- *Flower type*.—Actinomorphic, side facing with segments free.
- *Length*.—Approximately 1.4 cm, excluding tube. Tube length approximately 1 cm.
- *Diameter*.—Approximately 2.7 cm.
- *Petal quantity*.—6. Apex: pointed. Base: fused. Margin: Entire. Texture: Waxy. Petal Length: 1.5 cm. Petal Width: 0.5.

Color:

- *When opening*.—Inner surface: Near RHS Green 142B. Outer surface: Near RHS Red-Purple 63B.
- *Fully opened*.—Inner surface: Near RHS Green 142B. Outer surface: Near RHS Red-Purple 64B.
- *Fading*.—Inner surface: Near RHS Red-Purple 59A. Outer surface: Near RHS Red-Purple 59A.

Bud:

- *Shape*.—Oblong.
- *Length*.—1.4 cm.
- *Diameter*.—0.6 cm.
- *Color*.—Near RHS Yellow-Green 147B.

Terminal bracts:

- *Shape*.—Elliptic.
- *Length*.—Approximately 4.5 cm, excluding sheath.
- *Width*.—Approximately 1.3 cm.
- *Quantity*.—Average 17.
- *Tip*.—Pointed.
- *Base*.—Sheathing.
- *Margin*.—Entire. Color Upperside: Near RHS Red 49B, flushed and margin Red-Purple 59A. Color Underside: Near RHS Red 49B, flushed and margin Red-Purple 59A.

Pedicels:

- *Length*.—Approximately 2 cm.
- *Diameter*.—Approximately 0.2 cm.
- *Aspect*.—Approximately 45° angle to point of attachment, straight.
- *Strength*.—Strong , flexible.
- *Color*.—Near RHS Red-Purple 59B.

Scape:

- *Length*.—Approximately 65 cm.
- *Diameter*.—Approximately 1.6 cm.
- *Aspect*.—Approximately 90° angle to rosette.
- *Strength*.—Strong.
- *Color*.—Near RHS Red-Purple 59A.

REPRODUCTIVE ORGANS

Stamens:

- *Number*.—6.
- *Filament length*.—1 cm.

Anthers:

- *Length*.—1.1 cm.
- *Shape*.—Linear.
- *Color*.—Near RHS Yellow-Green 154C.
- *Pollen*.—Color: Near RHS Yellow-Green 154B. Quantity: Moderate.

Pistil:

- *Number*.—1.
- *Length*.—0.9 cm.

*Style*.—Length: 0.5 cm. Color: Near RHS Red-Purple 59A.

*Stigma*.—Shape: Conical. Color: Near RHS Yellow-Green 154C. Ovary Color: Near RHS Red-Purple 59A.

OTHER CHARACTERISTICS

Seeds and fruits:

*Description*.—Trilocular capsule. Irregular seed count, seeds small, approximately 0.1 cm, black, round.

*Fruit color*.—Near RHS Greyed-Purple 187B. Shiny, highly ornamental.

*Longevity*.—Approximately 10 weeks.

Disease/pest resistance: Good resistance to soil and foliage pathogens and pests common to *Eucomis* has been observed.

Temperature tolerance: The new variety exhibits a good temperature tolerance range for *Eucomis*. Good tolerance for temperatures between −5 to 35° C.

What is claimed is:

1. A new and distinct cultivar of *Eucomis* plant named 'EUW061' as herein illustrated and described.

* * * * *